US012788293B2

(12) United States Patent
Oh et al.

(10) Patent No.: US 12,788,293 B2
(45) Date of Patent: Nov. 10, 2026

(54) METHOD OF LABELING EMPATHY DATASET ACCORDING TO DEPRESSIVE DISORDER DIAGNOSTIC CRITERIA

(71) Applicants: SAMSUNG LIFE PUBLIC WELFARE FOUNDATION, Seoul (KR); RESEARCH & BUSINESS FOUNDATION SUNGKYUNKWAN UNIVERSITY, Suwon (KR)

(72) Inventors: Ha Young Oh, Seoul (KR); Seog Ju Kim, Seoul (KR); Geon Ju Lee, Suwon-si (KR); Da Bin Park, Pyeongtaek-si (KR)

(73) Assignees: SAMSUNG LIFE PUBLIC WELFARE FOUNDATION, Seoul (KR); RESEARCH & BUSINESS FOUNDATION SUNGKYUNKWAN UNIVERSITY, Suwon (KR)

( * ) Notice: Subject to any disclaimer, the term of this patent is extended or adjusted under 35 U.S.C. 154(b) by 120 days.

(21) Appl. No.: 18/820,738

(22) Filed: Aug. 30, 2024

(65) Prior Publication Data

US 2025/0072800 A1 Mar. 6, 2025

(30) Foreign Application Priority Data

Aug. 30, 2023 (KR) ........................ 10-2023-0114707

(51) Int. Cl.

*G06F 40/268* (2020.01)
*A61B 5/00* (2006.01)

(Continued)

(52) U.S. Cl.

CPC ............ *A61B 5/165* (2013.01); *A61B 5/0002* (2013.01); *G06F 40/242* (2020.01); *G06F 40/268* (2020.01); *G16H 50/20* (2018.01)

(58) Field of Classification Search

CPC ........ G06F 16/35; G06F 40/131; G06F 16/36; G06F 16/3329; G06F 16/31; G06F 40/35;

(Continued)

(56) References Cited

U.S. PATENT DOCUMENTS 11,544,795 B2 * 1/2023 Wang .................. G06F 16/3329
11,809,826 B2 * 11/2023 Ambati ................. G06F 40/279

(Continued)

FOREIGN PATENT DOCUMENTS

WO 2010105216 A2 9/2010

OTHER PUBLICATIONS

Gaur Manas et al: ""Let Me Tell You About Your Mental Health!" Contextualized Classification of Reddit Posts to DSM-5 for Web-based Intervention", Oct. 22, 2018 (Oct. 22, 2018), (Year: 2018).*
Yao et al., D4: a Chinese Dialogue Dataset for Depression-Diagnosis-Oriented Chat, Proceedings of the 2022 Conference on Empirical Methods in Natural Language Processing, 2022, pp. 2438-2459.

(Continued)

*Primary Examiner* — Abdelali Serrou
(74) *Attorney, Agent, or Firm* — STIP Law Group, LLC

(57) ABSTRACT

A labeling method according to an embodiment may include: receiving a consultation dataset sentence; classifying the consultation dataset sentence into morpheme units and extracting target data; searching whether the target data is included in each of a plurality of categories of a word dictionary; and labeling the consultation dataset sentence in the word dictionary based on a result of the searching.

8 Claims, 8 Drawing Sheets

(51) Int. Cl.

| | |
|---|---|
| ***A61B 5/16*** | (2006.01) |
| ***G06F 40/242*** | (2020.01) |
| ***G16H 50/20*** | (2018.01) |

(58) Field of Classification Search

CPC ...... G06F 40/56; G06F 40/268; G06F 40/242; G06F 40/216; G06F 40/20; G06F 40/22; G06F 40/30; G06F 40/44; G06F 21/6218; G06F 40/205; G06F 40/279; G06F 16/24575; G06F 16/355; G06F 16/2462; G06F 21/629; G06F 2216/03; G06F 40/174; G06F 16/353; G06F 16/90335; G06F 16/93; G06F 18/2431; A61B 5/165; G16H 50/20; G06N 20/00

See application file for complete search history.

(56) References Cited

U.S. PATENT DOCUMENTS

| | | | | |
|---|---|---|---|---|
| 12,517,984 | B1 * | 1/2026 | Vamvourellis | G06F 18/2415 |
| 2022/0068463 | A1 * | 3/2022 | Dolan | G06Q 10/40 |
| 2023/0048098 | A1 * | 2/2023 | Lam | G10L 25/63 |
| 2023/0186023 | A1 * | 6/2023 | Saillet | G06F 16/93 704/9 |
| 2025/0316362 | A1 * | 10/2025 | Watanabe | A61B 5/38 |

OTHER PUBLICATIONS

Li et al., Automatic Construction of a Depression-Domain Lexicon Based on Microblogs: Text Mining Study, Jmir Medical Informatics, 2020, pp. 1-17, vol. 8, Issue 6.

Office action from the Korean Intellectual Property Office (KIPO) concerning Application No. 10-2023-0114707, Mar. 16, 2026, English translation.

* cited by examiner

| | |
|---|---|
| 1 | PERSISTENT DEPRESSED MOOD MOST OF THE DAY, NEARLY EVERY DAY |
| 2 | MARKEDLY DECREASED INTEREST OR PLEASURE IN ALMOST ALL DAILY ACTIVITIES MOST OF THE DAY, NEARLY EVERY DAY |
| 3 | WEIGHT LOSS OR GAIN WITHOUT DIETING, DECREASED OR INCREASED APPETITE NEARLY EVERY DAY |
| 4 | INSOMNIA OR HYPERSOMNIA NEARLY EVERY DAY |
| 5 | MENTAL AGITATION OR RETARDATION NEARLY EVERY DAY |
| 6 | FATIGUE OR LOSS OF ENERGY NEARLY EVERY DAY |
| 7 | SIMPLE SELF-BLAME, FEELINGS OF WORTHLESSNESS OR INAPPROPRIATE GUILT NEARLY EVERY DAY |
| 8 | DECREASED THINKING AND CONCENTRATION, DIFFICULTY MAKING DECISIONS NEARLY EVERY DAY |
| 9 | RECURRENT THOUGHTS OF DEATH, RECURRENT SUICIDAL THOUGHTS OR ATTEMPTS WITHOUT PLAN, OR DETAILED PLAN TO ATTEMPT SUICIDE |

FIG. 2A

210 pd.DataFrame(ko_model.wv.most_similar('LONELY'))

| | 0 | 1 |
|---|---|---|
| 0 | GET BETTER | 0.996288 |
| 1 | JOB | 0.995594 |
| 2 | POUR | 0.995523 |
| 3 | RELAPSE | 0.995220 |
| 4 | REALLY | 0.995156 |
| 5 | MISCELLANEOUS | 0.995114 |
| 6 | CHORES ONLY | 0.994962 |
| 7 | FAINT | 0.994896 |
| 8 | FIX | 0.994891 |
| 9 | ETC | 0.994885 |

pd.DataFrame(ko_model.wv.most_similar('TERRIBLE'))

| | 0 | 1 |
|---|---|---|
| 0 | TIRED | 0.997162 |
| 1 | BLOWING | 0.996577 |
| 2 | LONELY | 0.996278 |
| 3 | CHANGE | 0.996089 |
| 4 | LONESOME | 0.995752 |
| 5 | MISS | 0.995708 |
| 6 | SOME | 0.995619 |
| 7 | FATAL | 0.995618 |
| 8 | BIG | 0.995615 |
| 9 | DIFFICULT | 0.995500 |

220

| | |
|---|---|
| 1 | : ['DEPRESSED', 'MOOD', 'SAD', 'HOPELESS', 'HELPLESS', 'WORTH', 'LESS''] |
| 2 | : ['DOWN'], ['FEEL', 'NO', 'EMOTION'], ['LACK OF', 'INSPIRATION'] |
| 3 | : ['HUNGRY'], ['STUFF'], ['SKIPPING', 'MEALS'], ['DIETING'], ['STODGY'] |
| 4 | : ['SLEEP', 'EARLY', 'MIDDLE', 'LATE'], ['NOT', 'SLEEPING', 'DEEPLY'] |
| 5 | : ['PERSON', 'NOTICEABLE', 'DEGREE', 'USUALLY', 'SPEECH', 'BEHAVIOR', 'SLOW'] |
| 6 | : ['GENERAL', 'PHYSICAL SYMPTOMS'], ['INVOLOVED'], ['HARD'], ['MUSCLE PAIN'] |
| 7 | : ['IT'S', 'MY', 'FAULT'], ['MY', 'SELF', 'DISAPPOINTED'], ['I', 'AM', 'HOPELESS'] |
| 8 | : ['DECISION-MAKING', 'DISORDER'], ['DIFFICULT', 'DECISION-MAKING'], ['CONTINUE', 'TO BE DIFFICULT'] |
| 9 | : ['SUICIDE', 'OR', 'SELF-HARM'], ['PAIN', 'WANTING TO', 'ESCAPE'] |

FIG. 4A

| MAJOR CATEGORIES | SEJONG PART OF SPEECH TAG | | SIM GWANG-SEOP PART OF SPEECH TAG | | KKMA SINGLE TAG V 1.0 | | | | | |
|---|---|---|---|---|---|---|---|---|---|---|
| | TAG | DESCRIPTION | CLASS | DESCRIPTION | GROUP1 | GROUP2 | TAG | DESCRIPTION | PROBABILITY TAG | STORAGE DICTIONARY |
| SUBSTANTIVE | NNG | COMMON NOUN | NN | NOUN | N | NN | NNG | COMMON NOUN | NNA | NOUN.DIC |
| | NNP | PROPER NOUN | | | | | NNP | PROPER NOUN | | |
| | NNB | DEPENDENT NOUN | NX | DEPENDENT NOUN | | | NNB | GENERAL BOUND NOUN | NNB | SIMPLE.DIC |
| | | | UM | UNIT NOUN | | | NNM | UNIT BOUND NOUN | | |
| | NR | NUMERIC | NU | NUMERIC | | NR | NR | NUMERIC | NR | |
| | NP | PRONOUN | NP | PRONOUN | | NP | NP | PRONOUN | NP | |
| PREDICATE | VV | VERB | VV | VERB | V | VV | VV | VERB | VV | VERB.DIC |
| | VA | ADJECTIVE | AJ | ADJECTIVE | | VA | VA | ADJECTIVE | VA | |
| | VX | AUXILIARY VERB | VX | AUXILIARY VERB | | VX | VXV | AUXILIARY VERB | VX | |
| | | | AX | AUXILIARY ADJECTIVE | | | VXA | AUXILIARY ADJECTIVE | | |
| | VCP | POSITIVE COPULA | CP | PREDICATIVE PARTICLE "IS" | | VC | VCP | POSITIVE COPULA, PREDICATIVE PARTICLE "IS" | VCP | RAW.DIC |
| | VCN | NEGATIVE COPULA | | | | | VCN | NEGATIVE COPULA, ADJECTIVE "NOT" | VCN | |
| DETERMINER | MM | DETERMINER | DT | GENERAL ADJECTIVE | M | MD | MDT | GENERAL ADJECTIVE | MD | SIMPLE.DIC |
| | | | DN | NUMBER ADJECTIVE | | | MDN | NUMBER ADJECTIVE | | |
| ADVERB | MAG | GENERAL ADVERB | AD | ADVERB | | MA | MAG | GENERAL ADVERB | MAG | |
| | MAJ | CONJUNCTIVE ADVERB | | | | | MAC | CONJUNCTIVE ADVERB | MAC | |
| EXCLAMATION | IC | EXCLAMATION | EX | EXCLAMATION | I | IC | IC | EXCLAMATION | IC | |

FIG. 4B

METHOD OF LABELING EMPATHY DATASET ACCORDING TO DEPRESSIVE DISORDER DIAGNOSTIC CRITERIA

CROSS-REFERENCE TO RELATED APPLICATIONS

This application claims the priority of the Korean Patent Applications NO 10-2023-0114707, filed on Aug. 30, 2023, in the Korean Intellectual Property Office. The entire disclosures of all these applications are hereby incorporated by reference.

BACKGROUND

1. Field

One or more embodiments relate to a method of labeling an empathy dataset according to depressive disorder diagnostic criteria.

2. Description of the Related Art

Fear due to negative social perception of mental disorders prevents counselees from receiving treatment for depressive disorder. Not only is there a shortage of counselors including psychiatrists, but there is also a lack of infrastructure to deal with depressive disorder accompanied by physical illness, making it difficult to respond in a timely manner. Accordingly, AI services based on natural language processing capable of providing timely counseling are emerging. Among them, chatbots, which are conversational recognition AI, may help with simple counseling by predicting the state of mental illness through text data of counselees. A chatbot refers to a robot that can converse with users. Natural language processing and machine learning tasks are essential to successfully conduct complex conversations. In this case, supervised learning is mainly used, and labeling a dataset is essential so that correct data may be used during learning.

In general, a machine learning model uses a labeled dataset to solve classification problems. In order for a machine learning model to learn and predict efficiently, a high-quality labeled dataset is required. There are several methods of labeling datasets, such as manual labeling and automatic labeling. First, manual labeling is a method of assigning datasets to experts and manually labeling them, which is highly accurate but expensive and time-consuming. Semi-supervised learning uses some manually labeled data and unlabeled data together to learn, which may reduce labeling costs but may result in incorrect labeling or omission.

SUMMARY

A labeling method according to an embodiment may include: receiving a consultation dataset sentence; classifying the consultation dataset sentence into morpheme units and extracting target data; searching whether the target data is included in each of a plurality of categories of a word dictionary; and labeling the consultation dataset sentence in the word dictionary based on a result of the searching.

The labeling the consultation dataset sentence may include labeling the consultation dataset sentence into a category corresponding to the target data. The extracting of the target data may include determining parts of speech, general adverbs, and noun prefixes corresponding to nouns, verbs, and roots as the target data in the consultation dataset sentence classified into the morpheme units.

The word dictionary may be generated based on DMS-5 depressive disorder diagnostic criteria.

The labeling the consultation dataset sentence may include determining similarity with the target data in each of the plurality of categories of the word dictionary when the target data is not included in the word dictionary; and labeling the consultation dataset sentence in the word dictionary when the similarity is equal to or greater than a preset threshold value.

According to an embodiment, the consultation dataset sentence may include a counselee utterance sentence and a counselor utterance sentence.

The labeling method according to an embodiment may further include training a depression counseling chatbot model based on the labeled data.

The training of the depression counseling chatbot model may include determining an answer to an input message based on the counselee utterance sentence.

BRIEF DESCRIPTION OF DRAWINGS

FIGS. 2A and 2B are views for explaining a method of generating a word dictionary according to an embodiment.

FIG. 4A is a view illustrating an example of classifying a consultation dataset sentence into morpheme units according to an embodiment.

FIG. 4B is a view illustrating an example of a part-of-speech tag table of a morphological analyzer according to an embodiment.

DETAILED DESCRIPTION

Hereinafter, embodiments of the present invention will be described with reference to the drawings. In the following description, descriptions of a well-known technical configuration in relation to a lead implantation system for a deep brain stimulator will be omitted. For example, descriptions of the configuration/structure/method of a device or system commonly used in deep brain stimulation, such as the structure of an implantable pulse generator, a connection structure/method of the implantable pulse generator and a lead, and a process for transmitting and receiving electrical signals measured through the lead with an external device, will be omitted. Even if these descriptions are omitted, one of ordinary skill in the art will be able to easily understand the characteristic configuration of the present invention through the following description.

Fear due to negative social perception of mental disorders prevents counselees from receiving treatment for depressive disorder. Not only is there a shortage of counselors including psychiatrists, but there is also a lack of infrastructure to deal with depressive disorder accompanied by physical illness, making it difficult to respond in a timely manner. Accordingly, AI services based on natural language processing capable of providing timely counseling are emerging. Among them, chatbots, which are conversational recognition AI, may help with simple counseling by predicting the state of mental illness through text data of counselees. A chatbot refers to a robot that can converse with users. Natural language processing and machine learning tasks are essential to successfully conduct complex conversations. In this case, supervised learning is mainly used, and labeling a dataset is essential so that correct data may be used during learning.

In general, a machine learning model uses a labeled dataset to solve classification problems. In order for a machine learning model to learn and predict efficiently, a high-quality labeled dataset is required. There are several methods of labeling datasets, such as manual labeling and automatic labeling. First, manual labeling is a method of assigning datasets to experts and manually labeling them, which is highly accurate but expensive and time-consuming. Semi-supervised learning uses some manually labeled data and unlabeled data together to learn, which may reduce labeling costs but may result in incorrect labeling or omission.

Hereinafter, a method of labeling an empathy dataset according to depressive disorder diagnostic criteria according to an embodiment will be described.

Figure 1:
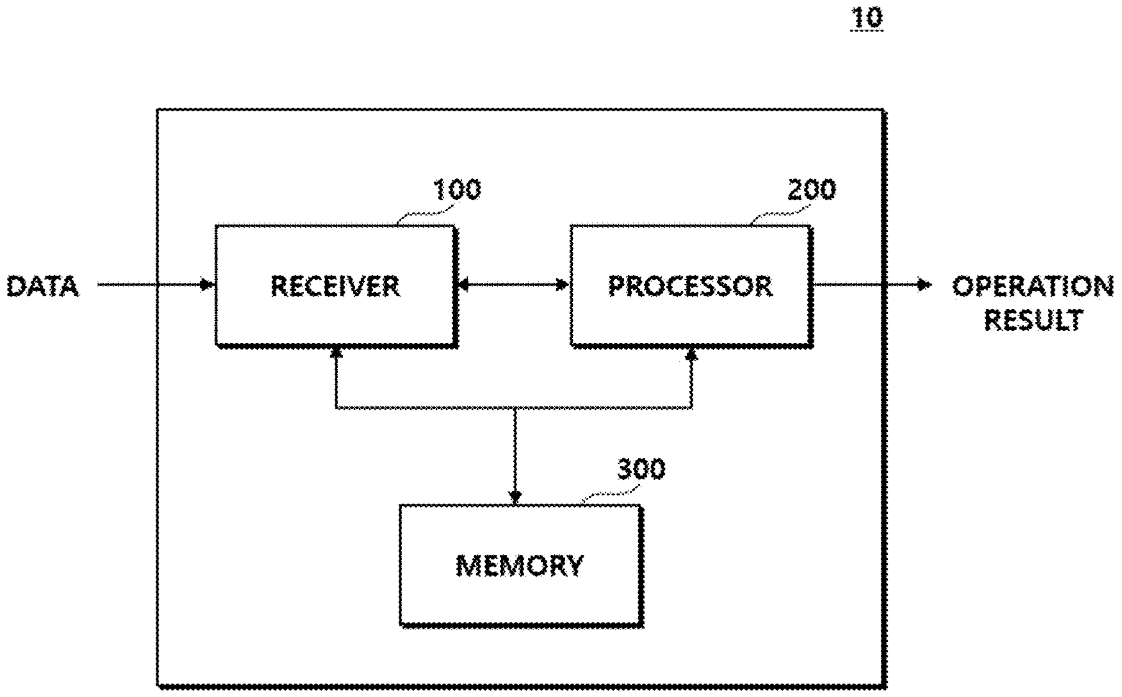
FIG. 1 is a schematic block diagram of a labeling device according to an embodiment.

FIG. 1 is a schematic block diagram of a labeling device according to an embodiment.

Referring to FIG. 1, a labeling device 10 may label a dataset using a word dictionary. The word dictionary may be generated based on DMS-5 depressive disorder diagnostic criteria. A method of generating a word dictionary according to an embodiment will be described in detail below with reference to FIGS. 2A and 2B. The labeling device 10 classifies and labels corresponding datasets using a word dictionary that classifies words expressing depressive disorder according to nine criteria.

The labeling device 10 is widely used in a medical field and may label a dataset using DSM-5 depressive disorder diagnostic criteria, which has proven expertise. A result of the labeling may be used to increase the accuracy of diagnosis through the corresponding dataset and a machine learning model in the medical field, and may be utilized in a depression counseling chatbot, etc. in a natural language processing field. In particular, in a chatbot field, the labeling device 10 also helps in eliciting positive chatbot evaluations because it shows an empathetic attitude toward a user by utilizing an empathy dataset and an actual consultation dataset.

The labeling device 10 includes a receiver 100 and a processor 200. The labeling device 10 may further include a memory 300.

The receiver 100 may include a receiving interface. The receiver 100 may receive a consultation dataset sentence.

The processor 200 may process data stored in the memory 300. The processor 200 may execute computer-readable code (e.g., software) stored in the memory 300 and instructions generated by the processor 200.

The processor 200 may be a data processing device implemented in hardware having a circuit with a physical structure for performing desired operations. For example, desired operations may include code or instructions included in a program.

For example, a data processing device implemented in hardware may be a microprocessor, a central processing unit, a processor core, a multi-core processor, a multiprocessor, an application-specific integrated circuit (ASIC), and a field programmable gate array (FPGA).

The processor 200 may classify the consultation dataset sentence into morpheme units and extract target data. The processor 200 may determine parts of speech, general adverbs, and noun prefixes corresponding to nouns, verbs, and roots as target data in the consultation dataset sentence classified into morpheme units.

The processor 200 may search whether the target data is included in each of a plurality of categories of the word dictionary, and label the consultation dataset sentence in the word dictionary based on search results.

The processor 200 may label the consultation dataset sentence in a category corresponding to the target data.

When the target data is not included in the word dictionary, the processor 200 may determine the similarity with the target data in each of the plurality of categories of the word dictionary, and may label the consultation dataset sentence in the word dictionary when the similarity is equal to or greater than a preset threshold value.

The memory 300 may store instructions (or programs) executable by the processor 200. For example, the instructions may include instructions for executing operations of the processor 200 and/or operations of each component of the processor 200.

The memory 300 may be implemented as a volatile memory device or a nonvolatile memory device.

The volatile memory device may be implemented as dynamic random access memory (DRAM), static random access memory (SRAM), thyristor RAM (T-RAM), zero capacitor RAM (Z-RAM), or twin transistor RAM (TTRAM).

The nonvolatile memory device may be implemented as electrically erasable programmable read-only memory (EEPROM), a flash memory, magnetic RAM (MRAM), spin-transfer torque (STT)-MRAM, conductive bridging RAM (CBRAM), ferroelectric RAM (FeRAM), phase change RAM (PRAM), resistive RAM (RRAM), nanotube RRAM, polymer RAM (PoRAM), nano floating gate memory (NFGM), a holographic memory, a molecular electronic memory device, or an insulator resistance change memory.

Figure 2B:
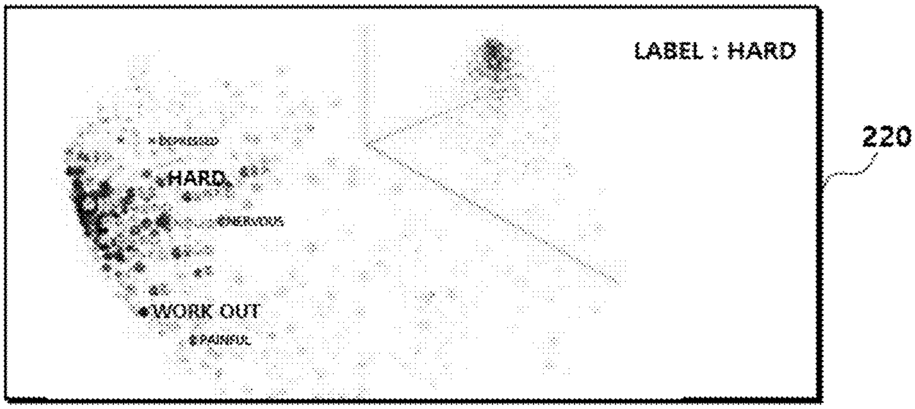

FIGS. 2A and 2B are views for explaining a method of generating a word dictionary according to an embodiment.

As described above, the word dictionary according to an embodiment may be generated based on DMS-5 depressive disorder diagnostic criteria.

The Diagnostic and Statistical Manual of Mental Disorders 5th Edition (DSM-5) is a mental disorder diagnostic classification system officially used by the American Psychiatric Association (APA). The DSM-5 is used all over the world, and depressive disorder is also included in the classification of mental disorders. Depressive disorder is determined by comprehensively considering nine diagnostic criteria of the DSM-5, the clinical experience of psychiatrists, clinical interviews, psychological test results, and treatment progress.

In Korea, the DSM-5 is also used to diagnose depressive disorder, but the lack of specialized personnel including psychiatrists and the negative social perception of depressive disorder prevents counselees from treating depressive disorder.

Referring to FIG. 2A, the DSM-5 has nine diagnostic criteria: 1) persistent depressed mood most of the day, nearly every day; 2) markedly decreased interest or pleasure in almost all daily activities most of the day, nearly every day; 3) weight loss or gain without dieting, decreased or increased appetite nearly every day; 4) insomnia or hypersomnia nearly every day; 5) mental agitation or retardation nearly every day; 6) fatigue or loss of energy nearly every day; 7) simple self-blame, feelings of worthlessness or inappropriate guilt nearly every day; 8) decreased thinking and concentration, difficulty making decisions nearly every day; and 9) recurrent thoughts of death, recurrent suicidal thoughts or attempts without a plan, or a detailed plan to attempt suicide.

A word dictionary according to an embodiment may be generated based on the DSM-5. In other words, the word dictionary may be composed of nine categories and words corresponding to the categories. For example, the category 3) 'weight loss or gain without dieting, decreased or increased appetite nearly every day' of the word dictionary may include words such as 'pig', 'fat', 'body weight', and 'appetite'. Furthermore, the words included in the word dictionary may be added according to a data augmentation algorithm.

Referring to FIG. 2B, the similarity of the words included in the word dictionary may be searched using Word2Vec. For example, in the case of Word2Vec hyperparameters, the window can be set to 5, allowing the prediction by using the 5 words to the left and right of the target word as context. In addition, min_count is a parameter that specifies the minimum frequency to be used in learning and is set to five times. Words that appear less than five times are excluded from learning. Finally, a CBOW algorithm is used by setting sg, a parameter that specifies an algorithm, to 0. Results of searching for words similar to 'lonely' and 'terrible' are as shown in Table 210. In addition, results of visualizing words similar to 'hard' are as shown in Table 220.

In FIGS. 2A and 2B, the word dictionary generated based on the DSM-5 is described as an example, but a method of generating the word dictionary is not limited to the above example. The word dictionary may be generated based on diagnostic criteria different from the DSM-5.

Figure 3:
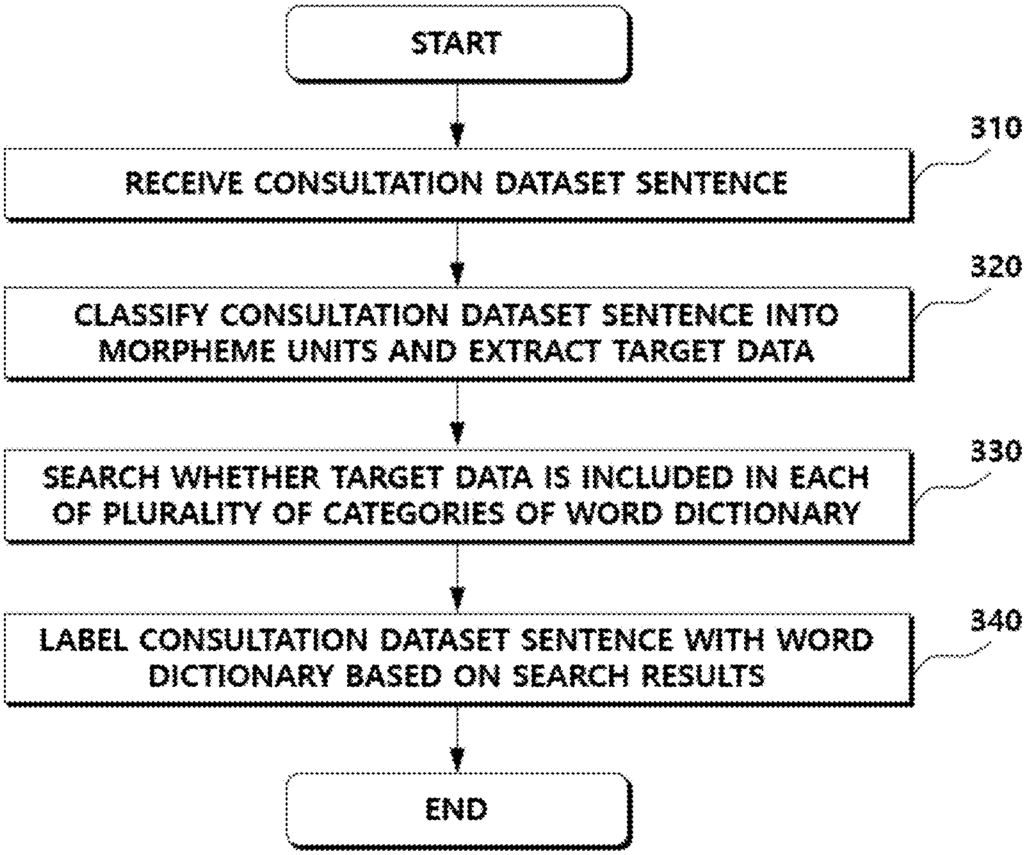
FIG. 3 is a flowchart for explaining a labeling method according to an embodiment.

FIG. 3 is a flowchart for explaining a labeling method according to an embodiment.

Referring to FIG. 3, operations 310 to 340 are described as being performed by the labeling device 10 described with reference to FIG. 1. However, these operations 310 to 340 may be used via any other suitable electronic device and within any suitable system.

In addition, operations of FIG. 3 may be performed in the illustrated order and manner, but the order of some operations may be changed or some operations may be omitted without departing from the spirit and scope of the illustrated embodiment. A number of operations shown in FIG. 3 may be performed in parallel or concurrently.

In operation 310, the labeling device 10 according to an embodiment may receive a consultation dataset sentence. The consultation dataset sentence is data related to mental health counseling and may be composed of a set of counselee utterance sentences and counselor utterance sentences.

The consultation dataset sentence may be, for example, 'wellness counseling data.' The wellness counseling data is data created by processing mental health counseling records. The wellness counseling data consists of 19 labels: depression, sadness, loneliness, anger, listlessness, emotional dysregulation, loss, decreased appetite, increased appetite, insomnia, nervousness, fatigue, guilt, decreased concentration, decreased self-confidence, decreased self-esteem, despair, suicidal impulse, and anxiety.

In operation 320, the labeling device 10 according to an embodiment classify the consultation dataset sentence into morpheme units and extract target data. Morpheme analysis refers to dividing sentences into morpheme units and identifying linguistic structures, and may distinguish between roots, prefixes, suffixes, and parts of speech.

FIG. 4A is a view illustrating an example of classifying a consultation dataset sentence into morpheme units according to an embodiment.

Referring to FIG. 4A, a morphological analyzer according to an embodiment may use an adjacent condition inspection method utilizing a pre-analyzed dictionary for speed, and a probabilistic model based on heuristics and a hidden Markov model (HMM) for quality. In the case of the heuristic model, morphemes may be analyzed by considering language characteristics such as part of speech of the previous word and part of speech of the next word. Afterwards, morphological analysis results are sorted to obtain the most appropriate information. The hidden Markov model is a probabilistic model that has a hidden state and an observed state, and the morphological analyzer may model each morpheme as a hidden state and the part of speech of the morpheme as an observed state. Through this, the probability of a morpheme appearing in a sentence may be estimated and morphological analysis may be performed.

The labeling device 10 according to an embodiment may determine parts of speech, general adverbs, and noun prefixes corresponding to nouns, verbs, and roots as target data in the consultation dataset sentence classified into morpheme units. The labeling device 10 may determine parts of speech, general adverbs, and noun prefixes corresponding to nouns, verbs, and roots as target data in the consultation dataset sentence classified into morpheme units by using a part-of-speech tag table of the morphological analyzer.

FIG. 4B is a view illustrating an example of a part-of-speech tag table of a morphological analyzer according to an embodiment.

Referring to FIG. 4B, the labeling device 10 may select only parts of speech, general adverbs, and noun prefixes corresponding to nouns, verbs, and roots in order to extract only words with specific meanings.

Referring again to FIG. 3, in operation 330, the labeling device 10 according to an embodiment may search whether target data is included in each of a plurality of categories of a word dictionary.

In operation 340, the labeling device 10 according to an embodiment may label the consultation dataset sentence with the word dictionary based on search results. The labeling device 10 may label the consultation dataset sentence with a category corresponding to the target data.

Figure 5:
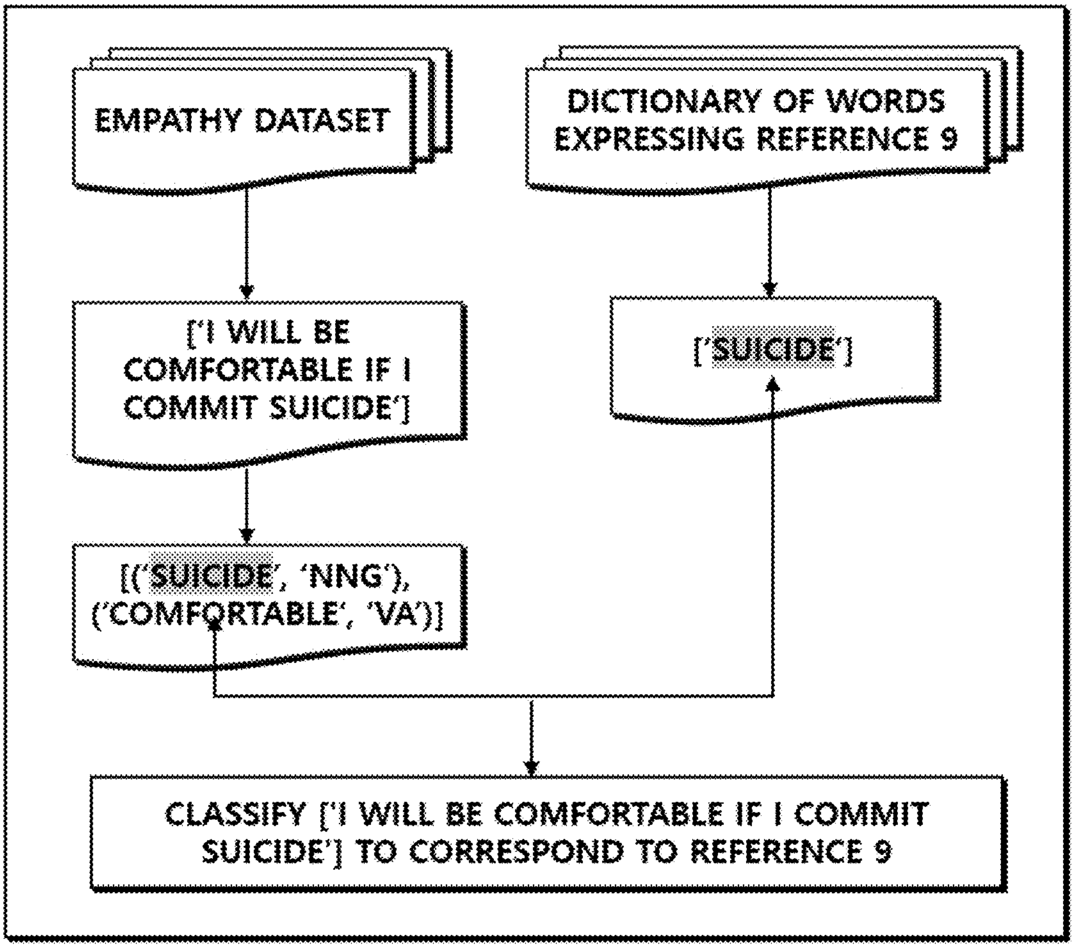
FIG. 5 is a view illustrating an example of a labeling method according to an embodiment.

FIG. 5 is a view illustrating an example of a labeling method according to an embodiment.

Referring to FIG. 5, the labeling device 10 according to an embodiment may receive 'I will be comfortable if I commit suicide' as an empathy dataset sentence, analyze morphemes of the sentence, and determine 'suicide', a common noun corresponding to a substantive, and 'comfortable', an adjective corresponding to a predicate, as target data from the consultation dataset sentence classified by morpheme units.

Afterwards, the labeling device 10 may determine whether the target data, 'suicide' and 'comfortable', exist in the word dictionary, and may label the sentence 'I will be comfortable if I commit suicide' to the word dictionary reference 9 based on the determination that 'suicide' exists in the word dictionary reference 9. The labeling device 10 may label not only the sentence 'I will be comfortable if I commit suicide' but also an empathy response sentence, which is a counselor sentence corresponding to the sentence 'I will be comfortable if I commit suicide.'

As another example, if 'pig' is included in the consultation dataset sentence in the word dictionary of 'weight loss or gain without dieting, decreased or increased appetite nearly every day', the labeling device 10 may label the corresponding sentence with the number 3.

In another embodiment, the labeling device according to an embodiment may label a sentence including target data if a word having a similarity that is equal to or greater than a preset threshold value exists, even if the same word as the target data is not searched in the word dictionary.

For example, assuming that 'Zhu Bajie' is determined as target data, if there is no word identical to 'Zhu Bajie' in the word dictionary reference 3, but there is a word (e.g., 'pig') with a similarity to 'Zhu Bajie' that is equal to greater than a preset threshold value, a sentence including 'Zhu Bajie' may be labeled with the number 3 in the word dictionary.

Alternatively, the labeling device 10 may label a sentence including target data if a word having a similarity equal to or greater than a preset first threshold value exists in a corresponding reference equal to or greater than a second threshold value, even if the same word as the target data is not searched in the word dictionary.

For example, assuming that 'Zhu Bajie' is determined as the target data, if there is no word identical to 'Zhu Bajie' in the word dictionary reference 3, but there are words (e.g., 'pig', 'fatty', 'chubby') that have a similarity to 'Zhu Bajie' equal to or greater than the preset first threshold value, and if there are at least the preset second threshold value (e.g., 3) of such words in the word dictionary reference 3, then a sentence including 'Zhu Bajie' can be labeled with the number 3 in the word dictionary.

The labeling device 10 may train a depression counseling chatbot model using data generated by the labeling method according to an embodiment. At this time, the labeling device 10 may determine an answer to an input message based on a counselee utterance sentence.

In more detail, as described above, a consultation dataset sentence according to an embodiment may include a counselee utterance sentence and a counselor utterance sentence. Even if target data is generated based on the counselor utterance sentence, the consultation dataset sentence including the counselee utterance sentence and the counselor utterance sentence may be the target of labeling. In other words, the labeling device may label the counselee utterance sentence corresponding to the counselor utterance sentence together.

Therefore, when training a depression counseling chatbot model using data generated by the labeling method, the labeling device 10 may be trained to determine a chatbot answer using the counselee utterance sentence. The counselee utterance sentence is an empathic answer, and may be particularly effective for AI chatbot answers.

Figure 6:
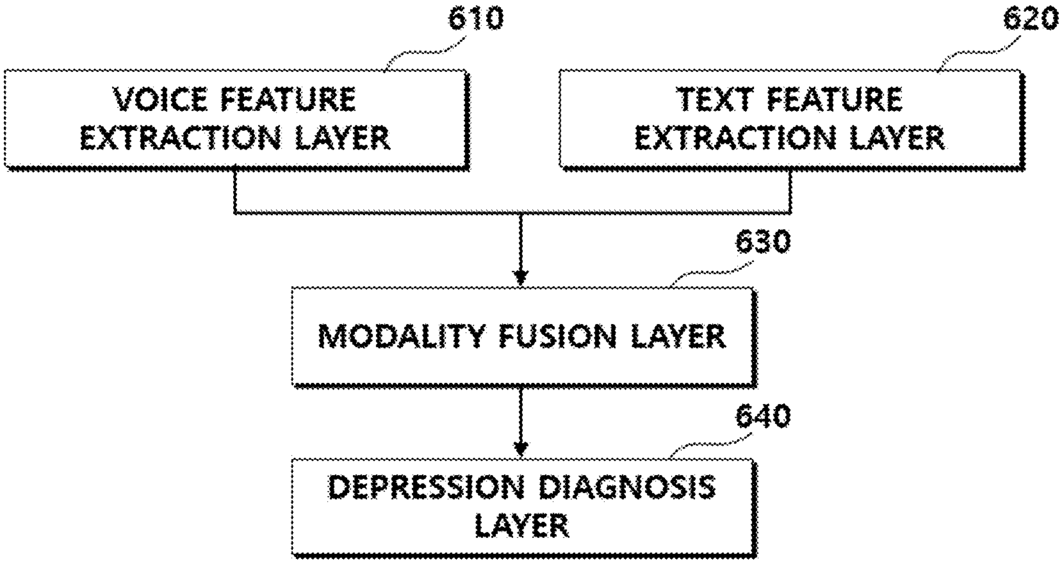
FIG. 6 is a view for explaining a depression diagnosis model using multimodal deep learning according to an embodiment.

FIG. 6 is a view for explaining a depression diagnosis model using multimodal deep learning according to an embodiment.

Referring to FIG. 6, the depression diagnosis model according to an embodiment may include a voice feature extraction layer 610, a text feature extraction layer 620, a modality fusion layer 630, and a depression diagnosis layer 640.

The voice feature extraction layer 610 according to an embodiment may be a layer that converts each speaker's voice into a digital signal and extracts features. The speaker's voice is a voice required to detect depression and may be the voice of a counselor.

The text feature extraction layer 620 according to an embodiment may be a layer that extracts features corresponding to a counselor's text. The text feature extraction layer 620 may be trained with training data generated by the labeling method described with reference to FIGS. 1 to 5.

The modality fusion layer 630 according to an embodiment may fuse an output of the voice feature extraction layer 610 and an output of the text feature extraction layer 620 using a tensor fusion network. The tensor fusion network may express features extracted from each modality as a single feature vector by connecting them to a fully connected layer. In this process, the voice and text features may be represented in a two-dimensional space by performing a two-layer Cartesian product operation. Because the two-layer Cartesian product calculates the product of all possible sets, it may capture correlations without information loss, and because the two-layer Cartesian product is a simple external operation, training parameters do not increase, so even if the dimension of features increases, the possibility of overfitting may not increase. The amount of operations may be reduced by using the tensor fusion network, and both the internal and external correlations between modalities may be considered.

The depression diagnosis layer 640 according to an embodiment may perform classification by connecting a final multimodal feature vector merged into one feature in the modality fusion layer 630 to an LSTM model. The LSTM model is a type of RNN model and may be used to complement shortcomings of RNN that does not reflect long-term memory when performing a task that requires a lot of context. Because it is reasonable to classify whether the subject is depressed or not by considering the entire context of an interview, LSTM may be used as the depression diagnosis layer 640 to add time-series characteristics. The function of an output layer may use sigmoid because a proposed model performs binary classification into two groups: 0, which is a group that does not show symptoms of depression, and 1, which is a group that shows symptoms of depression.

The embodiments described above may be implemented by hardware components, software components, and/or any combination thereof. For example, the devices, the methods, and components described in the embodiments may be implemented by using general-purpose computers or special-purpose computers, such as a processor, a controller, an arithmetic logic unit (ALU), a digital signal processor, a microcomputer, a field programmable gate array (FPGA), a programmable logic unit (PLU), a microprocessor, or any other devices which may execute and respond to instructions. A processing apparatus may execute an operating system (OS) and a software application executed in the OS. Also, the processing apparatus may access, store, operate, process, and generate data in response to the execution of software. For convenience of understanding, it may be described that one processing apparatus is used. However, one of ordinary skill in the art will understand that the processing apparatus may include a plurality of processing elements and/or various types of processing elements. For example, the processing apparatus may include a plurality of processors or a processor and a controller. Also, other processing configurations, such as a parallel processor, are also possible.

The software may include computer programs, code, instructions, or any combination thereof, and may construct the processing apparatus for desired operations or may independently or collectively command the processing apparatus. In order to be interpreted by the processing apparatus or to provide commands or data to the processing apparatus, the software and/or data may be permanently or temporarily embodied in any types of machines, components, physical devices, virtual equipment, computer storage mediums, or transmitted signal waves. The software may be distributed over network coupled computer systems so that it may be stored and executed in a distributed fashion. The software and/or data may be recorded in a computer-readable recording medium.

A method according to an embodiment may be implemented as program instructions that can be executed by various computer devices, and recorded on a computer-readable recording medium. The computer-readable recording medium may include program instructions, data files, data structures or a combination thereof. Program instructions recorded on the medium may be particularly designed and structured for embodiments or available to one of ordinary skill in a field of computer software. Examples of the computer-readable recording medium include magnetic media, such as a hard disc, a floppy disc, and magnetic tape; optical media, such as a compact disc-read only memory (CD-ROM) and a digital versatile disc (DVD); magneto-optical media, such as floptical discs; and hardware devices specially configured to store and execute program instructions, such as ROM, random-access memory (RAM), a flash memory, etc. Program instructions may include, for example, high-level language code that can be executed by a computer using an interpreter, as well as machine language code made by a complier.

In concluding the detailed description, those skilled in the art will appreciate that many variations and modifications may be made to the preferred embodiments without substantially departing from the principles of the present invention. Therefore, the disclosed preferred embodiments of the invention are used in a generic and descriptive sense only and not for purposes of limitation.

What is claimed is:

1. A computer-implemented labeling method performed by a labeling device including a receiver, a processor, and a memory storing a word dictionary having a plurality of categories corresponding to nine Diagnostic and Statistical Manual of Mental Disorders 5th Edition (DSM-5) depressive disorder diagnostic criteria, the method comprising:

receiving, through the receiver, a consultation dataset sentence included in wellness counseling data created by processing mental health counseling records, the consultation dataset sentence including a counselee utterance sentence and a counselor utterance sentence;

classifying, by the processor using a morphological analyzer and a part-of-speech tag table, the consultation dataset sentence into morpheme units and extracting target data by determining parts of speech, general adverbs, and noun prefixes corresponding to nouns, verbs, and roots;

searching, by the processor, whether the target data is included in each of the plurality of categories of the word dictionary;

when the target data is not included in the word dictionary, determining, by the processor using Word2Vec, a similarity between the target data and words included in each of the plurality of categories;

based on a result of the searching and the determining, labeling, by the processor, the consultation dataset sentence as labeled data into one of the plurality of categories, wherein (i) when the target data is included in the word dictionary, the consultation dataset sentence is labeled into a category corresponding to the target data, and (ii) when the target data is not included in the word dictionary, the consultation dataset sentence is labeled into a category including a word having the similarity equal to or greater than a preset threshold value, and wherein the labeling comprises labeling together the counselor utterance sentence and a counselee utterance sentence corresponding to the counselor utterance sentence; and training, by the processor, a depression counseling chatbot model based on the labeled data to determine an answer to an input message based on the counselee utterance sentence.

2. The method of claim 1, wherein the morphological analyzer uses an adjacent condition inspection method utilizing a pre-analyzed dictionary and a probabilistic model based on heuristics and a hidden Markov model.

3. The method of claim 1, wherein the plurality of categories correspond respectively to:

persistent depressed mood;

markedly decreased interest or pleasure;

weight loss or gain or appetite decrease or increase;

insomnia or hypersomnia;

mental agitation or retardation;

fatigue or loss of energy;

self-blame, worthlessness, or guilt;

decreased thinking or concentration or difficulty making decisions; and recurrent thoughts of death or suicide.

4. The method of claim 1, wherein, when the target data is extracted based on the counselor utterance sentence, the counselor utterance sentence and the counselee utterance sentence corresponding to the counselor utterance sentence are labeled together.

5. The method of claim 1, wherein determining the similarity comprises using Word2Vec configured with a window of 5, a minimum count of 5, and a continuous bag-of-words algorithm.

6. The method of claim 1, wherein, when the target data is not included in the word dictionary, the consultation dataset sentence is labeled into one category only when similarities between the target data and a plurality of words in the one category are each equal to or greater than a preset first threshold value and a number of the plurality of words is equal to or greater than a preset second threshold value.

7. The method of claim 1, wherein the depression counseling chatbot model determines the answer to the input message using the counselee utterance sentence as an empathic answer.

8. A non-transitory computer-readable recording medium storing instructions that, when executed by a processor of a labeling device including a receiver and a memory storing a word dictionary having a plurality of categories corresponding to nine depressive disorder diagnostic criteria set forth in the Diagnostic and Statistical Manual of Mental Disorders, Fifth Edition (DSM-5), cause the labeling device to perform operations comprising:

receiving, through the receiver, a consultation dataset sentence included in wellness counseling data created by processing mental health counseling records, the consultation dataset sentence including a counselee utterance sentence and a counselor utterance sentence;

classifying, by the processor using a morphological analyzer and a part-of-speech tag table, the consultation dataset sentence into morpheme units and extracting target data by determining parts of speech, general adverbs, and noun prefixes corresponding to nouns, verbs, and roots;

searching, by the processor, whether the target data is included in each of the plurality of categories of the word dictionary;

when the target data is not included in the word dictionary, determining, by the processor using Word2Vec, a similarity between the target data and words included in each of the plurality of categories;

based on a result of the searching and the determining, labeling, by the processor, the consultation dataset sentence as labeled data into one of the plurality of categories, wherein (i) when the target data is included in the word dictionary, the consultation dataset sentence is labeled into a category corresponding to the target data, and (ii) when the target data is not included in the word dictionary, the consultation dataset sentence is labeled into a category including a word having the similarity equal to or greater than a preset threshold value, and wherein the labeling comprises labeling together the counselor utterance sentence and a counselee utterance sentence corresponding to the counselor utterance sentence; and training, by the processor, a depression counseling chatbot model based on the labeled data to determine an answer to an input message based on the counselee utterance sentence.

* * * * *